United States Patent [19]

Smith

[11] Patent Number: 4,540,785
[45] Date of Patent: Sep. 10, 1985

[54] SUBSTITUTED HYDROQUINONES

[75] Inventor: Norman A. Smith, Hornchurch, England

[73] Assignee: Ciba-Geigy AG, Basel, Switzerland

[21] Appl. No.: 549,938

[22] Filed: Nov. 8, 1983

[30] Foreign Application Priority Data

Nov. 15, 1982 [GB] United Kingdom ............... 8232603

[51] Int. Cl.³ ................. C07D 491/048; C07D 307/88
[52] U.S. Cl. .................................... 546/116; 548/323; 548/370; 548/453; 549/299; 549/305
[58] Field of Search ............... 549/299, 305; 546/116; 548/323, 453, 370

[56] References Cited

PUBLICATIONS

Sloan et al., J. Org. Chem. (1983), vol. 48, pp. 3777–3783.

Primary Examiner—Henry R. Jiles
Assistant Examiner—Bernard I. Dentz
Attorney, Agent, or Firm—Joseph G. Kolodny

[57] ABSTRACT

Hydroquinones of the formula

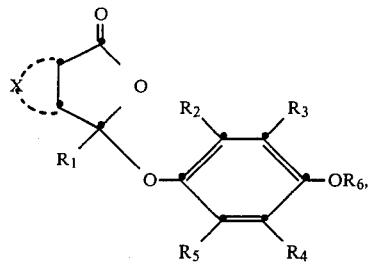

wherein X is the residue of a 5- or 6-membered ring, $R_1$ is hydrogen, alkyl or aryl, $R_1, R_3, R_4$ and $R_5$ are hydrogen or alkyl and $R_6$ is hydrogen or a group of the formula

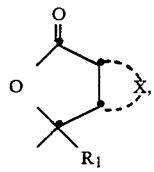

wherein X and $R_1$ are as defined above, are of use as protected developing agents in photographic silver halide material.

3 Claims, No Drawings

SUBSTITUTED HYDROQUINONES

This invention relates to substituted hydroquinones, to their preparation and use in photographic material.

Hydroquinone is the most widely used developing agent for developing latent silver images in silver halide photographic material. Most usually exposed photographic material is processed in a bath containing hydroquinone to develop the latent image but for some types of processing it is preferable that the hydroquinone is present already in the photographic material which after exposure is processed in an alkaline bath to develop the latent image as hydroquinone only acts as a developing agent under alkaline conditions. Such a method of processing is known as activation processing. Activation processing is extremely rapid but it is not widely employed except in certain special circumstances because the disadvantages of incorporating hydroquinone in the photographic material outweigh the advantages. These disadvantages include developer decomposition on ageing and interference with the setting and hardening of the gelatin or other colloidal layers in which it is incorporated during the coating of the photographic material. Further, activation processing often tends to cause stain and tanning of the processed material.

In an effort to overcome these disadvantages it has been proposed to use protected hydroquinones which are substituted hydroquinones in which the protecting group or groups are cleaved at the high pH-value of the alkaline processing bath. However, it has proved difficult to find substituted hydroquinones which are readily cleavable in the alkaline bath and thus which release the active hydroquinone quickly enough to achieve rapid processing and also substituted hydroquinones which are stable during coating and on storage of the photographic material. Many of the proposed substituted hydroquinone compounds contain in the protective moiety desensitising groups which limit the use of such compounds, or are coloured due to the presence of chromophoric groups, such as nitro groups, in the protective moiety. Such coloured compounds may be of use in certain circumstances, but their presence tends to cause speed losses in the photographic material.

Some of the proposed hydroquinone derivatives are water-insoluble and these compounds comprise comparatively bulky water-insolubilising groups which lead to high coating weights. The presence of high molecular weight components in a layer of photographic material often leads to poor inter-layer or layer/base adhesion and poor layer hardening. Examples of water-insoluble hydroquinone derivatives are given in Research Disclosure 16444 of December 1977.

We have now found a class of substituted hydroquinone compounds which are water-insoluble, cleave rapidly in alkaline solution and exhibit superior storage stability and little tendency to cause stain or tanning problems when material which contains them is activation processed. Furthermore, none of the compounds are coloured nor do they contain any desensitising groups, and all can be formulated easily in photographic layers.

According to the present invention there are thus provided substituted hydroquinone compounds of formula

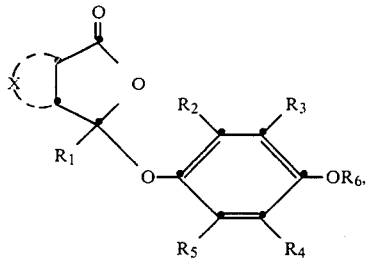

wherein X is the residue of a 5- or 6-membered ring, $R_1$ is hydrogen, optionally substituted alkyl or aryl, $R_2$, $R_3$, $R_4$ and $R_5$ are each hydrogen or alkyl having 1 to 4 carbon atoms, $R_6$ is hydrogen or a group of the formula

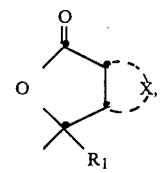

wherein $R_1$ and X have the meanings assigned to them above.

In the compounds of the formula (1), X denotes the atoms to complete a 5- or 6-membered ring. Aromatic rings thus formed are preferred. In particular, carbocyclic and N-heterocyclic 5- or 6-membered aromatic rings are preferred such as benzo, naphtho, pyrido, pyrazo, imidazolo and pyrrolo radicals, where benzo and pyrido are of special value.

$R_1$ is hydrogen or alkyl or aryl which both can be further substituted. Preferred alkyl groups $R_1$ are those having 1 to 4 carbon atoms such as methyl, ethyl, propyl, i-propyl, butyl or t-butyl. Methyl is more preferred. Suitable aryl groups $R_1$ are preferably phenyl and naphthyl rings. Especially good results are obtained if $R_1$ is phenyl.

The alkyl and aryl radicals $R_1$ just mentioned can be further substituted. Suitable further substituents in these radicals are halogen, preferably chlorine, bromine and iodine as well as carboxylic groups such as carboxylic acid (—COOH), carboxylic ester (—COOR, where R is alkyl having preferably 1 to 4 carbon atoms) and carboxylic amide (—CONH$_2$, —CONHR and —CON(R)$_2$, where R has the meaning just mentioned), and also alkyl, preferably methyl, ethyl, propyl or butyl, and aryl, preferably phenyl.

$R_2$, $R_3$, $R_4$ and $R_5$ are, independently of each other, hydrogen or alkyl which preferably contains 1 to 4 carbon atoms such as methyl, ethyl, propyl and butyl as well as the isomers i-propyl, t-butyl and 1- or 2-methylpropyl. Preferably, the above substituents are hydrogen or methyl.

$R_6$ is hydrogen or a group of the formula (2), wherein X and $R_1$ have the meaning assigned to them above. Preferably, $R_6$ is hydrogen.

In preferred hydroquinone compounds of the formula (1), $R_1$ is hydrogen, methyl or phenyl, $R_2$ to $R_6$ are each hydrogen and X completes a benzo or pyrido radical.

The compounds of the formula (1) may be prepared by reacting an intermediate compound of the formula

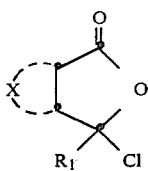

(3)

where $R_1$ and X have the meanings assigned to them above with a hydroquinone of the formula

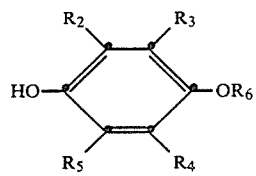

(4)

where $R_2$, $R_3$, $R_4$, $R_5$ and $R_6$ have the meanings assigned to them above, in an inert solvent, optionally in the presence of an organic base. Sometimes the organic base, for example pyridine, helps the reaction to proceed at a convenient speed. In other cases its presence is not necessary.

Suitable inert solvents are acetone and dimethylformamide. Usually, the reaction proceeds satisfactorily at room temperature but in other cases the reaction is carried out under reflux conditions.

According to another aspect of the present invention there is provided photographic silver halide material which comprises on a photographic support at least one colloid silver halide layer, there being present in the silver halide layer or in a layer in operative contact therewith a least one substituted hydroquinone compound of the formula (1).

By 'layer in operative contact therewith' is meant a layer which is close enough to the silver halide layer for the hydroquinone, released in this layer by the alkaline processing solution, to diffuse into the silver halide layer and there to develop the latent image.

Usually, silver halide photographic material which is to be activation processed comprises only one colloid silver halide layer and most usually this colloid is gelatin.

Therefore, according to another preferred embodiment of this aspect of the present invention, there is provided photographic silver halide material which comprises coated on a support a gelatino silver halide emulsion layer which comprises a substituted hydroquinone of the formula (1).

The amount of the compound of the formula (1) present in the silver halide photographic material will depend on the actual compound and on the proposed use of the photographic material. Preferably, however, the compound of the formula (1) is present in the photographic material in an amount within the range of 0.1 to 1.0 moles per 1.5 moles of silver halide present in the photographic material.

Preferably, the substituted hydroquinones of the formula (1) are dispersed in the layer of the photographic material as a solid dispersion which has been obtained by ball-milling the solid in an aqueous medium in the presence of a wetting agent. Alternatively, the water-insoluble compounds of the formula (1) may be dispersed in the layer of the photographic material in an oil, for example tricresyl phosphate.

The silver halide present in the photographic material may be any one of the normally employed silver halides such as silver chloride, silver bromide, silver chlorobromide, silver bromoiodide and silver iodochlorobromide.

The silver halide emulsions may be optically sensitised by the presence therein of optical sensitising dyes, for example merocyanine or carbocyanine dyes.

This silver halide emulsions may contain any of the additives commonly used in photographic emulsions, for example wetting agents such as polyalkylene oxides, stabilising agents such as tetraazaindenes, metal sequestering agents and growth or crystal habit modifying agents commonly used for silver halide, such as adenine.

Preferably, the colloid medium is gelatin or a mixture of gelatin and a water-soluble latex for example a latex of a vinyl acrylate-containing polymer. Most preferably, if such a latex is present in the final emulsion, it is added after all crystal growth has occurred. However, other water-soluble colloids, for example casein, polyvinylpyrrolidone or polyvinyl alcohol, may be used alone or together with gelatin.

The support may be any one of the supports normally used for photographic materials including paper base, polyethylene-coated paper base, oriented and subbed polyethylene terephthalate, cellulose triacetate, cellulose acetate butyrate, polystyrene and polycarbonate.

The photographic material of the present invention may be used in a large number of different ways including black and white print material, X-ray film material, colour film material, microfilm products and direct positive material.

The photographic material of the present invention most usually is prepared by forming an aqueous colloid coating solution of the silver halide which comprises a dispersion of the compound of the formula (1) and this colloid coating solution is coated as a layer on a support and dried.

After exposure the photographic material may be treated with an activator solution which is an aqueous alkaline solution which comprises for example sodium hydroxide or sodium carbonate. Most usually, the activator solution will have a pH-value of between 10 and 14. Stabilisers, antifoggants and development accelerators may also be present in the activator solution. The activator solution may be applied to the exposed photographic material of the present invention in all the usual ways such as surface application, total immersion of the material in the activator solution and spraying.

After the photographic material of the present invention has been activator processed it may be fixed in a silver halide fixing solution, for example ammonium thiosulphate, to remove the undeveloped silver halide, or it may be stabilised to render the remaining silver halide light-insensitive by treatment with a known stabiliser treatment solution, for example an aqueous ammonium thiocyanate solution.

The following examples will serve to illustrate the invention

EXAMPLE I

Preparation of the compound of the formula

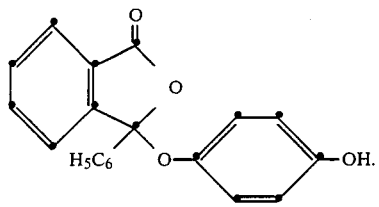

(a) Intermediate Compound 11.3 g o-Benzylbenzoic acid is treated carefully with 12.5 ml thionyl chloride and the mixture warmed to 50°–60° C. for three hours with stirring. Excess thionyl chloride is evaporated in vacuum and the residue is vacuum distilled to give 8.4 g of a yellow oil, (boiling point (0.77 mm): 169°–177° C.) which crystallises on storage at room temperature. The intermediate compound thus formed has the formula

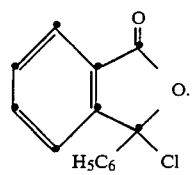 (3a)

(b) Compound of the formula (A)

3.7 g compound of the formula (3a) and 1.81 g hydroquinone are dissolved in 15 ml acetone. After a few minutes stirring at room temperature a white solid precipitates. The mixture is stirred for a further three hours then cooled in ice, the solid filtered and washed with a little acetone to give 3.8 g rough product (melting point: 195°–200° C.). Recrystallisation from acetone affords 2.85 g of the compound of the formula (A) as a white solid (melting point: 212°–213° C.).

Other compounds prepared similarly are those of the formulae:

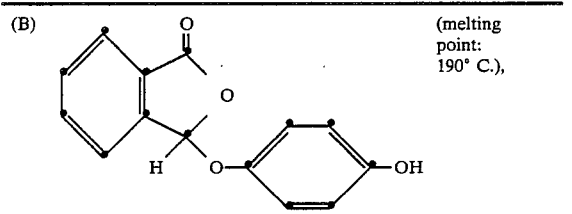 (B) (melting point: 190° C.),

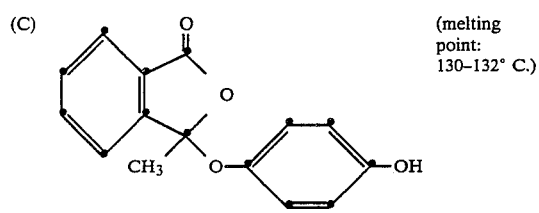 (C) (melting point: 130–132° C.)

and

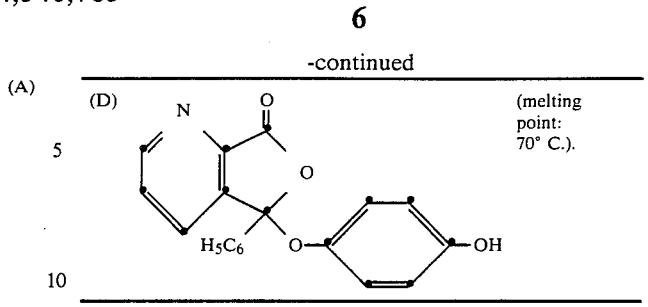 (D) (melting point: 70° C.).

Similar reaction of hydroquinone with the above-mentioned intermediate compound in the molar ratio of 1 to 2 (or excess of said intermediate compound) leads to the compounds of the formula

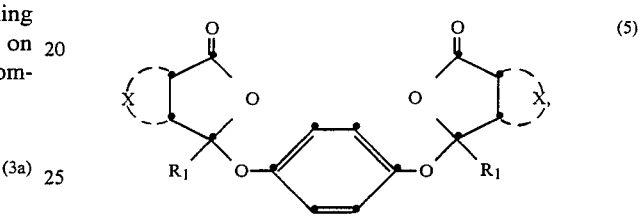 (5)

wherein $R_1$ and X have the meanings assigned to them above.

The compound of the formula

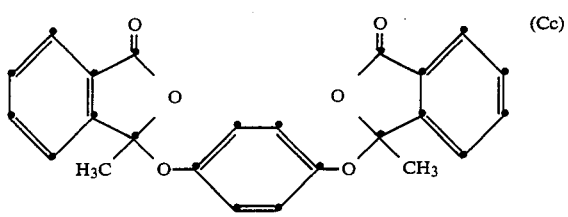 (Cc)

is prepared as follows:

The intermediate chloro compound of the formula

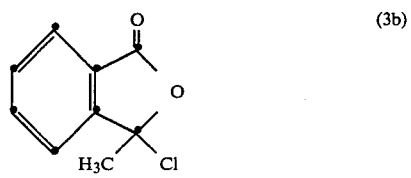 (3b)

is prepared in a similar manner as described above for compound of the formula (3a). This chloro compound of the formula (3b) (4.77 g) is added to hydroquinone (0.72 g) in acetone (50 ml) and pyridine (3 ml) in acetone (20 ml) is added simultaneously with cooling on an ice bath. The mixture is stirred for 2½ hours while being allowed to warm to room temperature, and then added to ice (100 g). An oil formed, which is extracted with dichloromethane, dried and evaporated to yield a white solid (2.57 g) which has a melting point of above 360° C.

According to this method, the compounds of the following formulae can be prepared:

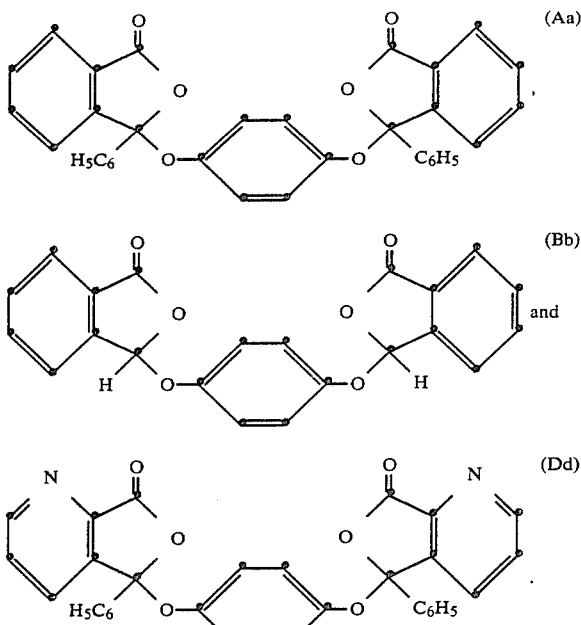

EXAMPLE II

Preparation of Solid Dispersion of Compound of Formula (A)

The following mixture is prepared:

400 mg compound of the formula (A), 0.25 ml 30% anionic wetting agent, 6.0 ml distilled water and 15 g 2 mm glass beads.

The above ingredients are added to a 25 ml beaker and milling is effected by agitating the glass beads with a propellor rotating at 1000 rpm for six hours. At the end of this time the glass beads are removed by filtration.

An aqueous coating solution of the dispersed compound of the formula (A) is coated on a triacetate base attached to a 2.43 dm² glass plate. The solution comprises:

200 mg compound of the formula (A) as the solid dispersion to produce a coating weight of 80 mg/dm², 0.90 ml silver chlorobromide gelatino emulsion to produce a coating weight of 25 mg/dm², 0.50 ml of a 10% gelatin solution to produce a total coating weight of 80 mg/dm², 1.0 ml of 1% aqueous formaldehyde solution and water to 10 ml.

The solution is coated at 40° C. on the triacetate base, set at 5° C. and dried. Then similar coatings of the compounds of the formulae B, C and D are prepared. Further, there is also prepared a coating of a comparative compound according to Research Disclosure 16444 (December 1977) which has the formula

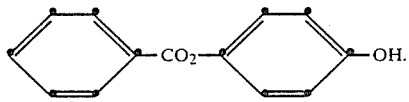

The coatings are tested by exposing in an overall manner and then treating with an activator solution comprising a 2 molar aqueous solution of sodium hydroxyde for both five and twenty seconds. After fixing in an ammonium thiosulphate bath (82 g/l) for one minute the coatings are washed then dried and the silver densities measured.

The following $D_{max}$-values are obtained:

TABLE

| compound | 5 second activation | 20 second activation |
| --- | --- | --- |
| A | 1.03 | 2.13 |
| B | 2.31 | 2.53 |
| C | 2.24 | 2.53 |
| D | 3.41 | 3.76 |
| E (comparison) | 0.00 | 1.00 |

The results show the much higher $D_{max}$-values on both long and short processing times by use of the novel compounds according to the present invention compared with those given by the compound of the formula (E). Higher $D_{max}$-values denote a more effective developer action.

I claim:

1. A substituted hydroquinone of formula

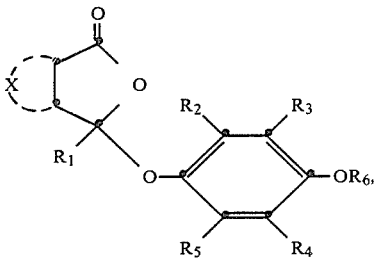

wherein

X represents the atoms to complete a benzo, naphtho, pyrido, pyrazo, imidazolo or pyrrolo radical, $R_1$ is hydrogen, alkyl having 1 to 4 carbon atoms, phenyl or naphthyl, these radicals being unsubstituted or substituted by chlorine, bromine, iodine, —COOH, —COOR, —CONHR or —CON(R)$_2$ wherein R is alkyl having 1 to 4 carbon atoms, $R_2$, $R_3$, $R_4$ and $R_5$ are each hydrogen or alkyl having 1 to 4 carbon atoms, $R_6$ is hydrogen or a group of the formula

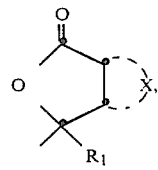

wherein $R_1$ and X have the meanings assigned to them above.

2. A hydroquinone according to claim 1, wherein $R_2$, $R_3$, $R_4$ and $R_5$ are independently of each other hydrogen or methyl.

3. A hydroquinone according to claim 1, wherein X represents the atoms to complete a benzo or pyrido radical, $R_1$ is hydrogen, methyl or phenyl, and $R_2$, $R_3$, $R_4$, $R_5$ and $R_6$ are hydrogen.

* * * * *